(12) United States Patent
Lakkireddy et al.

(10) Patent No.: US 10,722,244 B2
(45) Date of Patent: Jul. 28, 2020

(54) CARDIAC IMPLANTABLE ELECTRONIC DEVICE POCKET COMPRESSION APPARATUS AND METHOD OF MITIGATING LOCALIZED BLEEDING USING SAME

(71) Applicants: Dhanunjaya Lakkireddy, Leawood, KS (US); Srijoy Mahapatra, Edina, MN (US)

(72) Inventors: Dhanunjaya Lakkireddy, Leawood, KS (US); Srijoy Mahapatra, Edina, MN (US)

( * ) Notice: Subject to any disclaimer, the term of this patent is extended or adjusted under 35 U.S.C. 154(b) by 143 days.

(21) Appl. No.: 15/292,697

(22) Filed: Oct. 13, 2016

(65) Prior Publication Data
US 2017/0100130 A1      Apr. 13, 2017

Related U.S. Application Data

(60) Provisional application No. 62/240,967, filed on Oct. 13, 2015.

(51) Int. Cl.
| | | |
|---|---|---|
| *A61B 17/132* | (2006.01) | |
| *A41D 13/12* | (2006.01) | |
| *A61B 17/12* | (2006.01) | |

(52) U.S. Cl.
CPC ...... *A61B 17/1325* (2013.01); *A41D 13/1245* (2013.01); *A61B 2017/12004* (2013.01)

(58) Field of Classification Search
CPC .............. A61B 17/1325; A61B 17/132; A61B 2017/12004; A61B 17/1322;
(Continued)

(56) References Cited

U.S. PATENT DOCUMENTS 5,235,975 A   8/1993   Gang et al.
5,843,008 A   12/1998  Gerhard
(Continued)

FOREIGN PATENT DOCUMENTS

CN   202051904 U   11/2011
CN   202722580 U   2/2013
(Continued)

OTHER PUBLICATIONS

Israel Patent Office, International Search Report with Written Opinion, International Application No. PCT/US2016/056813, 12 pages, dated Jan. 26, 2017.
(Continued)

*Primary Examiner* — Katrina M Stransky
(74) *Attorney, Agent, or Firm* — Knobbe, Martens, Olson & Bear, LLP (57) ABSTRACT

A method mitigates pocket bleeding and hematoma formation in a patient by providing a pliable wrap having a solid block coupled with the wrap, and then securing the pliable wrap around the torso of the patient to align the solid block with the located localized torso area. The solid block at least in part covers the localized torso area. The wrap is secured to cause the wrap to apply a force, to the solid block, that produces a corresponding pressure on the localized torso area. The force applied to the solid block is high enough to cause the pressure to hinder blood flow to the localized torso area to promote clotting at the localized torso area. At the same time, the force applied to the solid block is low enough to cause the pressure to permit blood flow to the localized torso area to promote healing.

17 Claims, 8 Drawing Sheets

(58) Field of Classification Search
CPC ......... A41D 13/1245; A61F 2007/0231; A61F 5/30; A61F 5/32; A61H 2205/084
See application file for complete search history.

(56) References Cited

U.S. PATENT DOCUMENTS

| | | | |
|---|---|---|---|
| 6,155,996 | A | 12/2000 | Van Brunt et al. |
| 7,316,658 | B2 | 1/2008 | Gagne |
| 8,430,830 | B1 | 4/2013 | Ariza |
| 2005/0182344 | A1* | 8/2005 | Dixon ............... A61F 5/30 602/1 |
| 2008/0132820 | A1* | 6/2008 | Buckman ........... A61B 17/1325 602/48 |
| 2008/0319473 | A1 | 12/2008 | Rosenbaum |
| 2010/0228171 | A1 | 9/2010 | Waldridge |
| 2013/0085427 | A1 | 4/2013 | Malhi |
| 2013/0110019 | A1 | 5/2013 | Hopman et al. |
| 2014/0107546 | A1 | 4/2014 | Falconio-West et al. |
| 2015/0073317 | A1* | 3/2015 | Cox ................... A61F 5/30 601/84 |
| 2015/0085425 | A1 | 3/2015 | Xiao et al. |
| 2015/0305958 | A1* | 10/2015 | Hoff .................. A61B 17/1325 601/134 |
| 2016/0095755 | A1* | 4/2016 | Joyner ............. A61F 13/00068 606/202 |

FOREIGN PATENT DOCUMENTS

| | | |
|---|---|---|
| GB | 2329590 A | 3/1999 |
| WO | WO 2016/001802 A1 | 1/2016 |

OTHER PUBLICATIONS

Martin-Casañas et al., "Cardiac device infections is associated with pocket hematoma and diabetes mellitus: The role of the cardiovascular nurse," International Journal of Cardiology, vol. 171, pp. e5-e7, Jan. 15, 2014.

Mott et al., "The bulk modulus and Poisson's ratio of "incompressible" materials," Journal of Sound and Vibration, vol. 312, pp. 572-575, 2008.

Warfield et al., "Elastic constants of Bulk Polymers," Naval Ordnance Laboratory, White Oak, Silver Spring, Maryland, NOLTR 71-226, 14 pages, Apr. 12, 1972.

Supplementary European Search Report for Application No. EP 16 85 6179 dated May 31, 2019

* cited by examiner

FIG. 1
Outer Surface

Folded, Front View (RHS)
Not to scale

FIG. 5

Folded, Rear View (RHS)
Not to scale

CARDIAC IMPLANTABLE ELECTRONIC DEVICE POCKET COMPRESSION APPARATUS AND METHOD OF MITIGATING LOCALIZED BLEEDING USING SAME

PRIORITY

This patent application claims priority from provisional U.S. patent application No. 62/240,967, filed Oct. 13, 2015, entitled, "Implantable Cardiac Device Pocket Compression Apparatus," and naming Dhanunjaya Lakkireddy and Srijoy Mahapatra as inventors [practitioner's file 4179/1001], the disclosure of which is incorporated herein, in its entirety, by reference.

TECHNICAL FIELD

The invention generally relates to a medical apparatus and, more particularly, the invention relates to a treatment apparatus for use in connection with cardiac device implantations.

BACKGROUND ART

Several hundred thousands of patients receive subcutaneous cardiac devices (pacemakers, defibrillators, resynchronization therapy devices, loop recorders) throughout the world each year, with many thousands in the United States alone. With increasing advances in medical devices and the advent of life saving implantable cardioverter defibrillators along with cardiac resynchronization therapy, cardiac device therapy placed in the chest through the infraclavicular/subclavian approach has become very common. Usually, after sterile preparation, a small incision is made below the clavicle either on the right or left side. A subcutaneous pocket is created, bleeders are secured, and access to the subclavian vein or cephalic vein is obtained under the guidance of fluoroscopy. Then pacing or defibrillator leads may be placed in the appropriate chambers of the heart. These leads may be secured to the fascia over the pectoralis muscle and the end of which may be usually plugged into the ports in the device generator. The portion of the leads and the generator may be placed in the pocket and closed in two or three layers of suture. Bleeders may be secured before closing the pocket. Sterile strips may be placed over the closed incision and allowed to heal over the next few days.

Based on prior research, pocket bleeding and hematoma formation may be seen in about 4.9% patients and the incidence may be higher in those receiving defibrillators compared to pacemakers. Pocket bleeding can prolong hospital stay in 1.5% of patients who receive these devices up to 2.5 days with about 0.5% requiring repeat hospitalization and close to 1% needing pocket revision and hematoma evacuation. The risk of post device bleeding and hematoma formation may be significantly higher (e.g., up to 12%-20%) in those patients who may be bridged with anticoagulants like heparin and enoxaparin. Even in those cases where warfarin is continued throughout the procedure, the risk of post procedural bleeding may be up to 2-6%. Often, large hematomas and subsequent evacuations lead to increased incidence of infection.

Commonly, small swelling or hematoma left untreated and healing are left to normal body processes. However, hematomas and pocket bleeding can be serious enough in a certain percentage of patients as described above, requiring immediate attention. This can significantly increase the cost of treatment, and the amount of lost wages. This can also add a significant morbidity to the patient's health. Patients with device site hematomas and bleeding are at higher risk for infections which often require hospitalizations, intravenous antibiotic therapy and device extraction that leads to significant procedural risks, costs and patient comfort

SUMMARY OF ILLUSTRATIVE EMBODIMENTS

In accordance with one embodiment of the invention, a medical device for applying pressure to a localized area of patient's body includes a pliable wrap for wrapping around at least a portion of the patient, and a block of solid, non-inflatable material positioned between the wrap and the localized area of the patient. The wrap may be a vest for holding the block against the patient's torso, or a sleeve to hold the block against a patient's arm or a leg, to name but a few examples. In some embodiments, the wrap includes an elastic material, such as neoprene for example, and may also include straps to adjust the pressure applied to a localized area on the patient by the block.

The block is sized and shaped to apply pressure to the localized area of the patient, which pressure is sufficient to hinder but not completely prevent blood flow in the localized area of the patient's body. For example, the block may have a wedge shape with a narrow face positioned to face the patient when the medical device is worn by the patient.

Some embodiments include a sealable pouch in the medical device for securing the block in position, and some embodiments also include an absorbent sheath around the block within the pouch. Moreover, some embodiments include at least one filler member within the pouch to secure the location of the block within the pouch. Other embodiments secure the block with one or more straps, or a hook-and-loop fastener such as Velcro.

In accordance with another embodiment of the invention, a method of mitigating pocket bleeding and hematoma formation in a patient locates a localized torso area of the patient that may be subject to bleeding and/or hematoma formation. The localized torso area is at least in part covered by a bandage and/or dressing. Next, the method provides a pliable wrap having a non-inflatable solid block coupled with the wrap, and then secures the pliable wrap around the torso of the patient to align the solid block with the located localized torso area. The solid block is secured between at least a portion of the wrap and the bandage and/or dressing, at least in part covering the localized torso area. The wrap is secured to cause the wrap to apply a force, to the solid block, that produces a corresponding pressure on the localized torso area. The force applied to the solid block is high enough to cause the pressure to hinder blood flow to the localized torso area to promote clotting at the localized torso area. At the same time, the force applied to the solid block is low enough to cause the pressure to permit blood flow to the localized torso area to promote healing.

BRIEF DESCRIPTION OF THE DRAWINGS

Those skilled in the art should more fully appreciate advantages of various embodiments from the following description discussed with reference to the drawings summarized immediately below.

DETAILED DESCRIPTION OF SPECIFIC EMBODIMENTS

Illustrative embodiments mitigate pocket bleeding and hematoma formation in a patient by providing constant, adjustable pressure to a localized area of the patient's body. To that end, a mechanical, noninvasive garment has adjustable levels of compression to treat and/or substantially reduce the likelihood of hematomas from cardiac devices, such as pacemakers, defibrillators, loop recorders, and pressure monitoring systems placed underneath the skin in the human chest/torso. Among other configurations, the garment may be formed as a single unit with straps, and includes a compression block in a pouch of the garment. During use, the block applies specific pressure to a targeted area of the patient. The garment may be worn in a similar manner to a jacket, i.e., over the shoulder that is closest to the cardiac device. A first shoulder strap can be adjusted for appropriate contact, while a second strap (e.g., around the chest) may be adjusted to selectively apply pressure to the block, consequently applying pressure to the targeted area. Illustrative embodiments may be used over a device pocket (formed in a patient's body), which may have a hematoma, or may be used in a prophylactic fashion to avoid (or at least substantially reduce the likelihood that) a hematoma when they are expected.

During use, the patient may move around without being limited to a bed or chair. The garment also may enable the patient to carry on activities of daily living with minimal limitation. Accordingly, the garment may decrease the incidence of hematoma formation after device implantation, especially when device implantation was done while the patient was on therapeutic anticoagulation. For patients on anticoagulants (e.g., heparin or enoxaparin), the garment may be used immediately after device implantation until the patient's anticoagulation levels settle to a prescribed therapeutic range. Also, the garment can compress a hematoma of the pocket that has already formed. As a result, the garment may reduce pain and suffering for the patient, decrease duration of hospitalization, decrease recurrent hospitalizations and additional interventions (e.g., reopening the device pocket and hematoma evacuations). Consequently, the garment potentially can reduce significant health care costs. Details of illustrative embodiments are discussed below.

Figure 1:
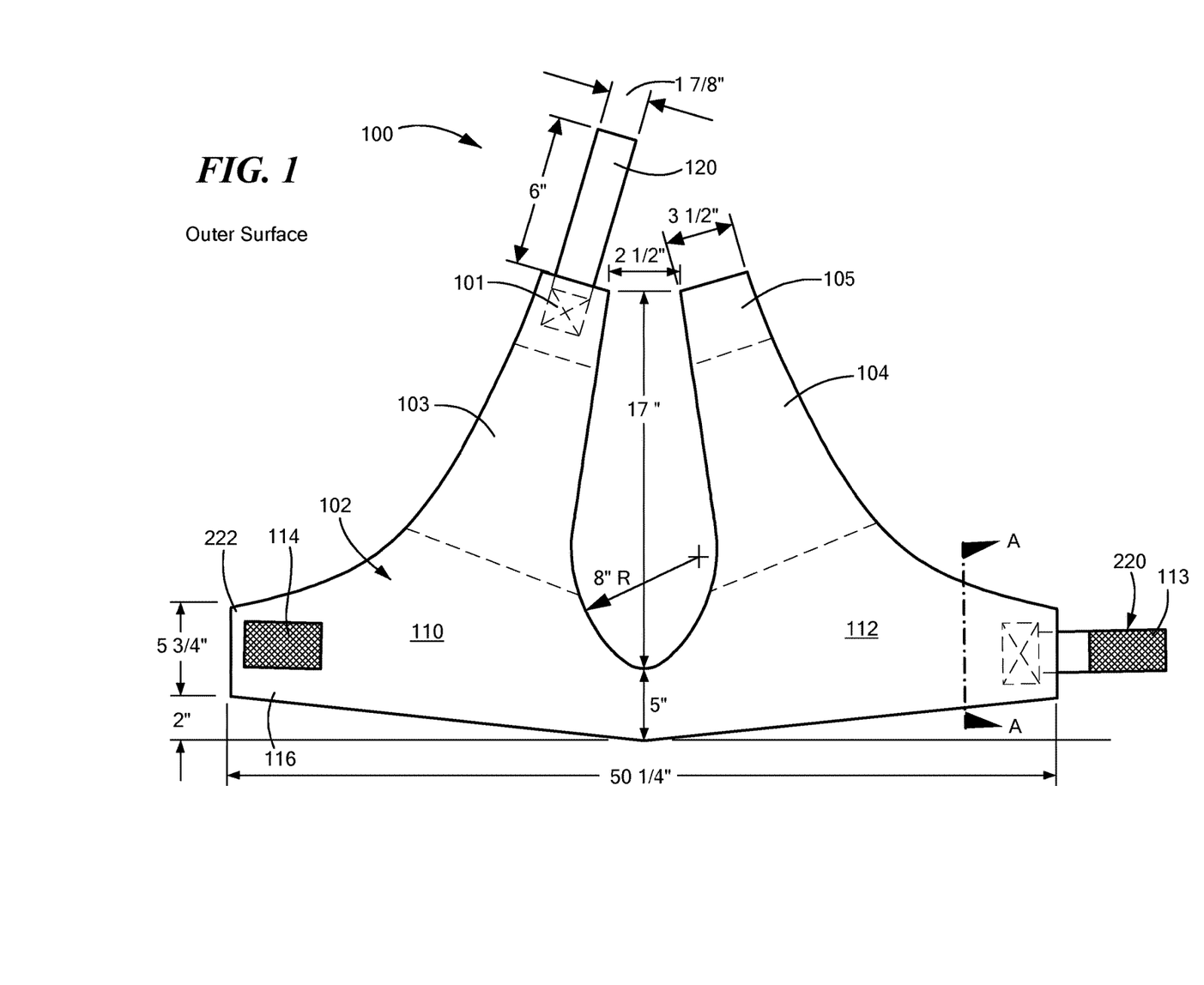
FIG. 1 schematically illustrates a front view of the outer surface of a compression vest in a detached configuration in accordance with illustrative embodiments.
Figure 2:
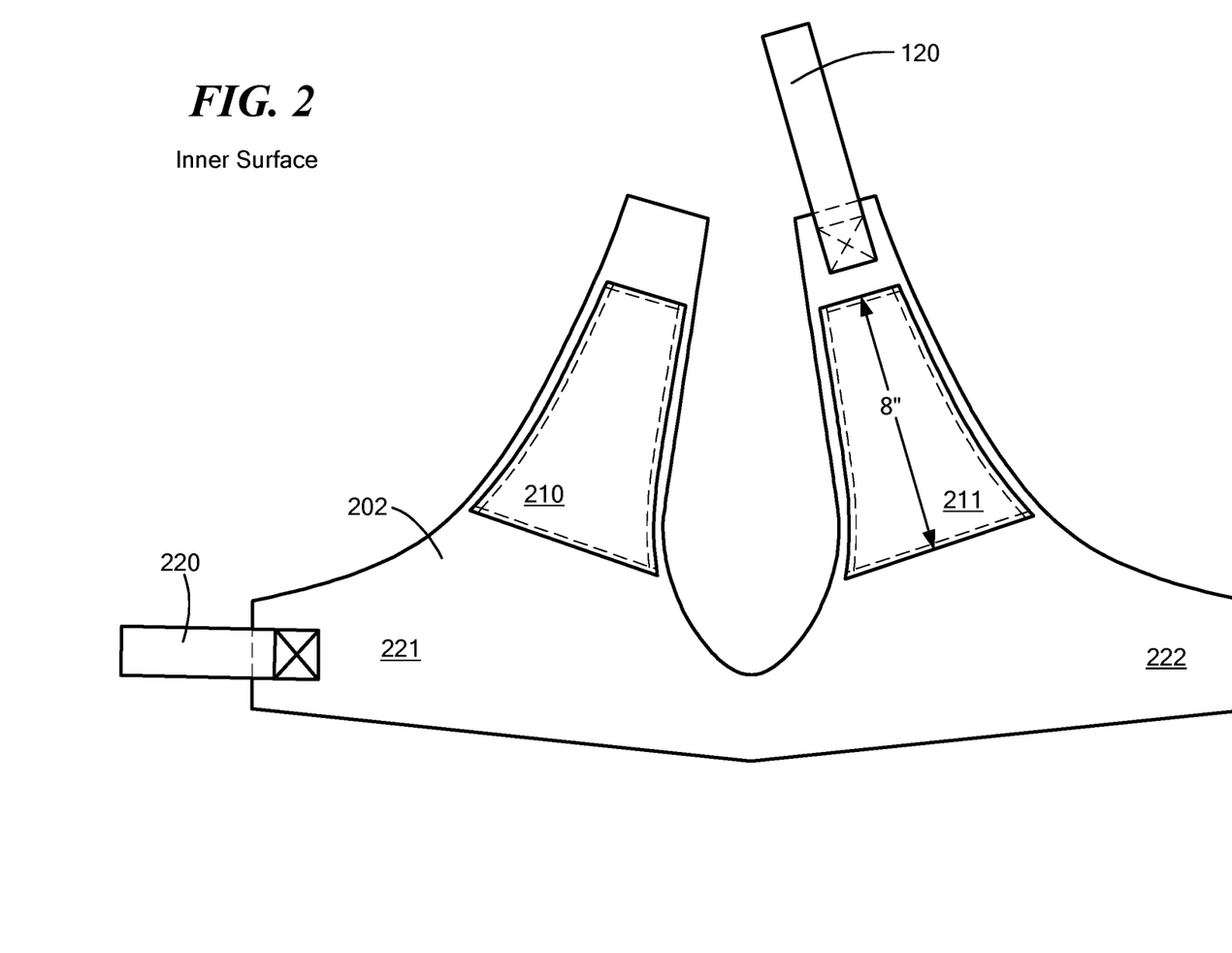
FIG. 2 schematically illustrates a rear view of the inner surface of a compression vest in a detached configuration in accordance with illustrative embodiments.

FIGS. 1 and 2 respectively show front and rear views of illustrative embodiments of a garment or vest 100 in a detached configuration. It should be noted that the specific dimensions in the drawing are exemplary only and thus, are not intended to limit various illustrative embodiments. FIGS. 6B and 6C schematically illustrate front and rear views, respectively, of a vest 100 worn by a patient.

The vest 100 is a single structure configured to anchor over the patient's shoulder and wrap around (e.g., form a loop around) the patient's upper chest in a circumferential fashion.

The vest 100 includes a waist band 110 configured to wrap around the patient's torso and secure the vest 100 to the patient. To that end, the waist band 110 includes a waist strap 220 coupled to a back flap 221. The waist strap 220 includes a hook and loop patch 113 (e.g., Velcro) configured to removably and adjustably couple to a counterpart hook and loop patch 114 on a front flap 222. The waist strap 220 may be useful in adjusting the top-to-bottom stretch and compression of the vest 100.

The vest 100 also includes left and right shoulder portions 101 and 105 extending from the waist band 110. In use, when worn by a patient, the left and right shoulder portions 101 and 105 are physically coupled by a shoulder strap 120, to secure the vest 100 around the patient's shoulder. For example, the strap 120 may go over the ipsilateral shoulder connecting the scapular portion 105 to the pectoral 101 portion of the vest.

Together, the shoulder strap 120 and waist strap 220 provide stretch and compression of the vest 100 in four directions (e.g., left and right across the patient's torso, and up and down relative to the patient's shoulders).

The vest 100 also includes at least one structure (e.g., 210; 211) for securing a compression block 700 (described below) to the vest 100. In illustrative embodiments, the structure 210; 211 may be a pouch, or sealable pouch, to hold the compression block 700. In some embodiments, the structure 210; 211 may include straps, belts, hook and loop fasteners, or other devices.

More specifically, a pouch 210 holds the compression block 700 adjacent to an area on a patient's body where pressure is desired. In illustrative embodiments, the pouch 210, 211 is on or in the inner surface 202 of the vest 100, so that the vest 100 presses the block 700 towards the patient.

Chest pads 103 and/or 104 hold a compression block 700 on the incision site (650) on patient's chest. In some embodiments, chest pad 103 and/or 104 of the vest 100 may have a surface that is larger than their respective pouches 210, 211. Moreover, the chest pads 103 and 104 provide a surface for applying a compressive force to the compression block 700 inside a pouch 210, 211. The amount of compressive force applied by chest pads 103 and 104 to the compression block 700 may be adjusted using a shoulder strap 120 and/or a waist strap 220.

Some embodiments may come pre-attached at the shoulder strap and can be worn around the shoulder like a sling. Such embodiments may omit the waist band 110 and its strap 220.

Figure 3A:
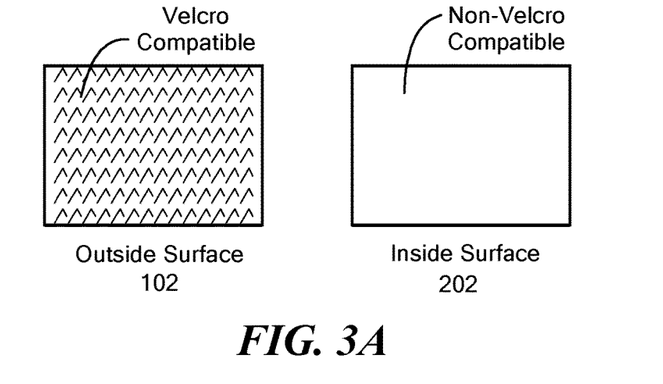
FIG. 3A schematically illustrates details of a fabric for a compression vest in accordance with illustrative embodiments.

The vest 100 includes a stretchable body (e.g., waist strap 110 and/or shoulder portions 101 and 105) made up of stretchy or elastic materials, such as 2 mm thickness SBR Neoprene VELCRO compatible UBL finish, for example. In addition, as schematically illustrated in FIG. 3A, such materials may be waterproof and/or insulated. Moreover, the outer surface 102 of the vest may be VELCRO compatible and the inner surface 101 may be smooth and impervious to water.

Figure 3B:
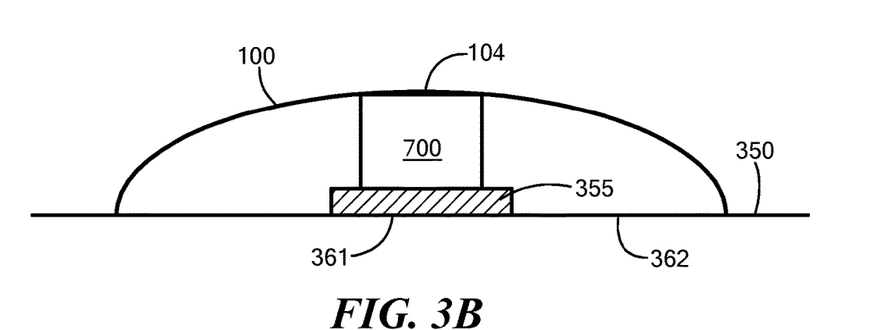
FIG. 3B schematically illustrates a compression block urged towards a patient's body by a garment.

FIG. 3B schematically illustrates a compression block 700 urged against a patient's body 350 by the stretchy material of a vest 100. In the embodiment of FIG. 3B, a bandage or dressing 355 is positioned between the compression block 700 and the patient 350. When worn by a patient, tension in the material of the vest 100 imparts a force to the compression block 700. The amount of the force may be adjusted by adjusting the straps 120 and/or 220. In addition, the amount of the force may be a function of the elastic properties and/or tightness of the material of the vest 100, in that the more the vest material is stretched, the greater the force it applies to the compression block 700. As discussed below, this force produces a pressure to the patient's body 350 (e.g., a portion of the patient's torso).

That force is high enough to cause the pressure to hinder blood flow to the localized torso area. Specifically, in illustrative embodiments, this pressure eventually aids in causing capillaries in the local area under pressure to coagulate, thus reducing and eventually stopping bleeding from the site. In addition, this pressure also preferably is low enough to mitigate the effect of a hematoma in that localized area. While a sufficiently high pressure is desired, such pressure also preferably is low enough to permit blood flow to the localized torso area. Accordingly, while reducing blood to the area to stop bleeding, blood still flows to the area to promote tissue health. As discussed below, a medical professional preferably can select the appropriate pressure to meet these competing demands.

Figure 3C:
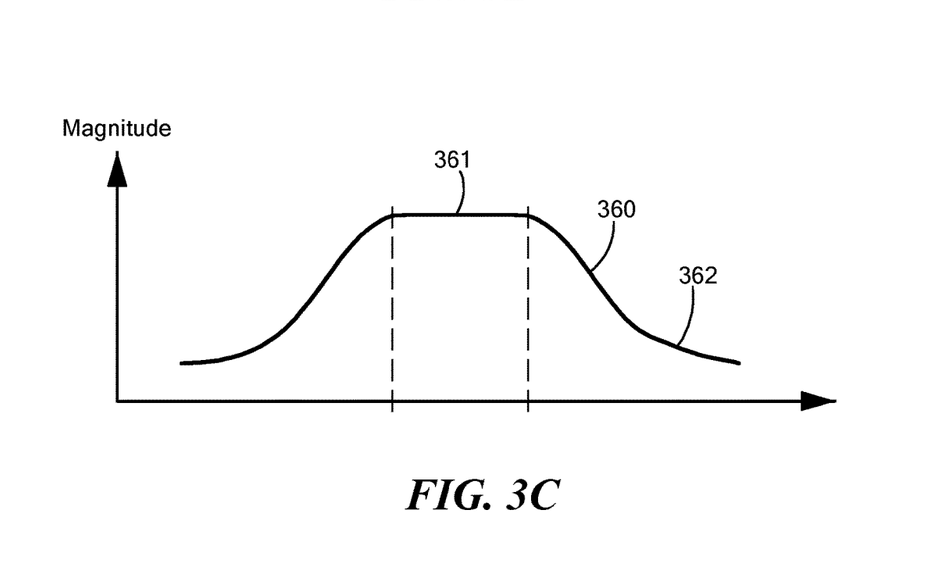
FIG. 3C schematically illustrates pressure gradient within a patient.

The amount, location and gradient of the applied force may influence the efficacy of the vest 100. For example, as schematically by the compression gradient line 360 illustrated in FIG. 3C, the compression applied by the compression block 700 is high immediately beneath the compression block 700, but dissipates with distance from the block. The relatively high compression beneath the compression block 700 (e.g., at point at point 361), and relatively lower compression away from the block (e.g., at point 362) forces fluids within a hematoma or pocket outward from under the compression block 700. The structure of the compression block 700 directly impacts efficacy. Specifically, the inventors recognized that a solid compression block 700 produces a better-defined gradient than, for example, a bladder, which can be inflated. Accordingly, illustrative embodiments of the vest 100 and its compression block 700 should be beneficial to a patient with either or both a hematoma, and a high risk for pocket hematoma.

Specifically, various embodiments may be useful, for example, to:

1. Patients undergoing cardiac device implantation (pacemakers, cardioverter defibrillators, cardiac resynchronization therapy pacemakers & defibrillators, loop recorders, cardiac chamber pressure monitors) and chemotherapy ports who develop bleeding into the pocket and hematoma, 2. Patients who may be on antiplatelet and or anticoagulation therapy and may be at high risk for bleeding and hematoma formation, 3. Patients who may be on bridging therapy with heparin or enoxaparin immediately after cardiac device implantation for mechanical prosthetic valves, deep venous thrombosis, high risk atrial fibrillation patients, intracardiac thrombi etc., 4. Patients who may be high risk for bleeding into pocket—elderly, renal failure, prolonged intervention, prior device extraction, pocket revisions, bleeding disorders etc., and/or 5. Patients who had a cardiac implantable electronic device ("CIED") placed and developed a hematoma that needs that needs further care.

Figure 4:
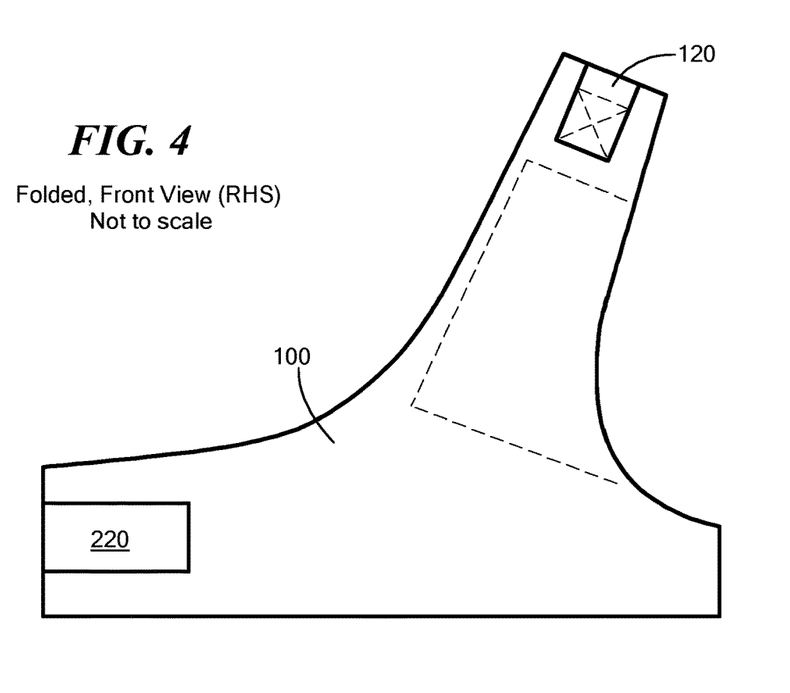
FIG. 4 schematically illustrates a front view in an attached configuration in accordance with illustrative embodiments.
Figure 5:
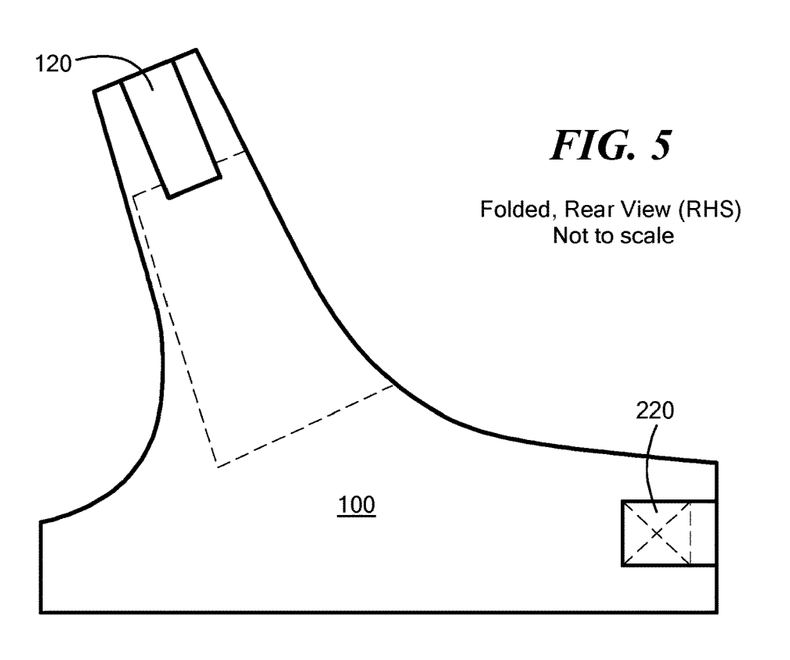
FIG. 5 schematically shows a rear view in an attached configuration in accordance with illustrative embodiments.

FIG. 4 and FIG. 5 show that the fabric pad may be folded approximately at its middle.

Figure 6A:
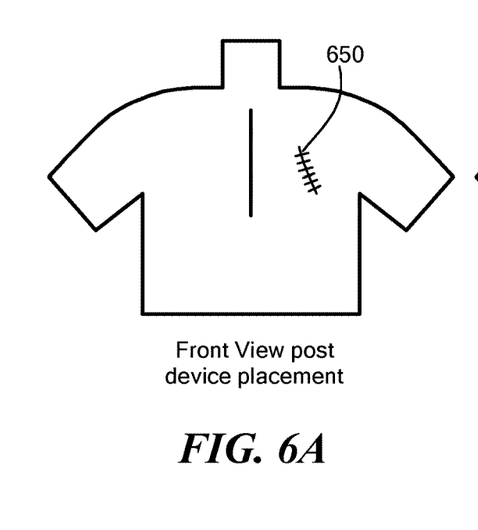
FIGS. 6A-6B schematically illustrate an incision on the chest of a patient.
Figure 6B:
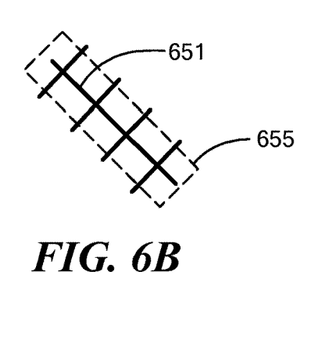
Figure 6C:
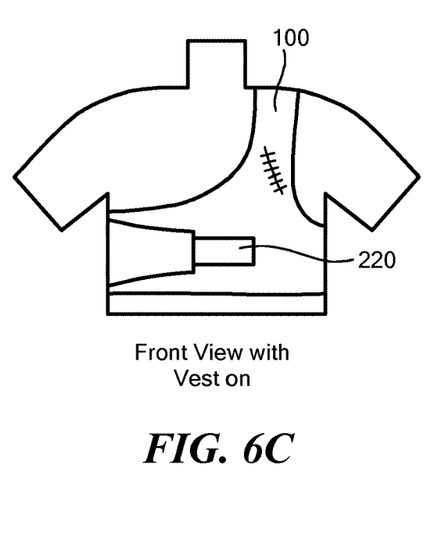
FIGS. 6C-6D schematically illustrate a front view in an attached configuration on a patient and a rear view in an attached configuration on a patient, respectively, in accordance with illustrative embodiments.

FIG. 6A, FIG. 6B and FIG. 6C schematically illustrate the patient with an incision 650 dressed on the left hand side of the body. FIG. 6B schematically illustrates a localized area 655 defined at least in part by the area where a compression block 700 meets a patient's body. For example, FIG. 6B schematically illustrates a localized area 655 near a patient's incision 650 and suture 651.

Figure 6D:
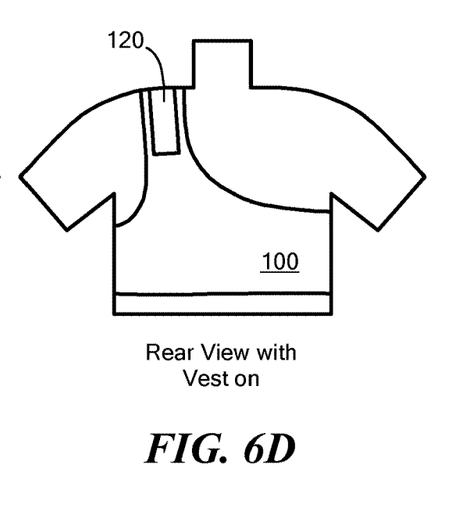

FIG. 6C schematically shows a front view in an attached configuration on the patient, while FIG. 6D shows a rear view of the vest 100 in an attached configuration on the patient. In some embodiments, from the front of the patient, the apparatus may be dressed on the patient and may approximately look like the front view illustrated in FIG. 6C. From the back of the patient, the dressed apparatus may approximately look like the rear view illustration in FIG. 6D. In other embodiments, the incision may be dressed on the right hand side of the body. In some embodiments, the adjustments described in reference to FIG. 1 may also be made when the vest is on the patient.

Figure 7A:
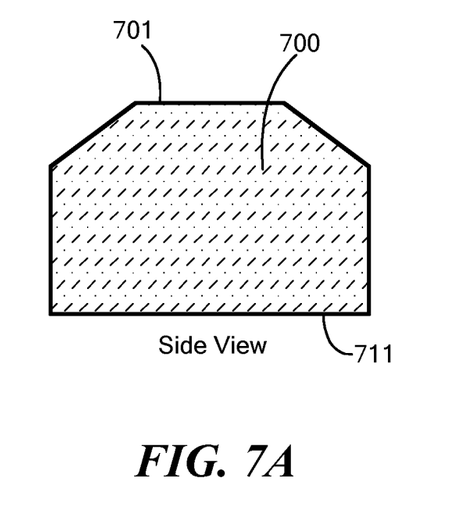
FIGS. 7A-7D schematically illustrate embodiments of compression blocks for use with a compression garment in accordance with illustrative embodiments.
Figure 7B:
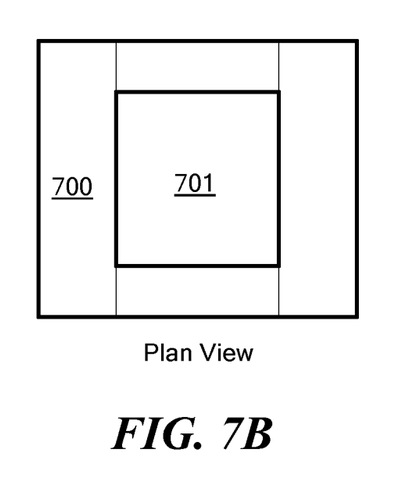
Figure 7C:
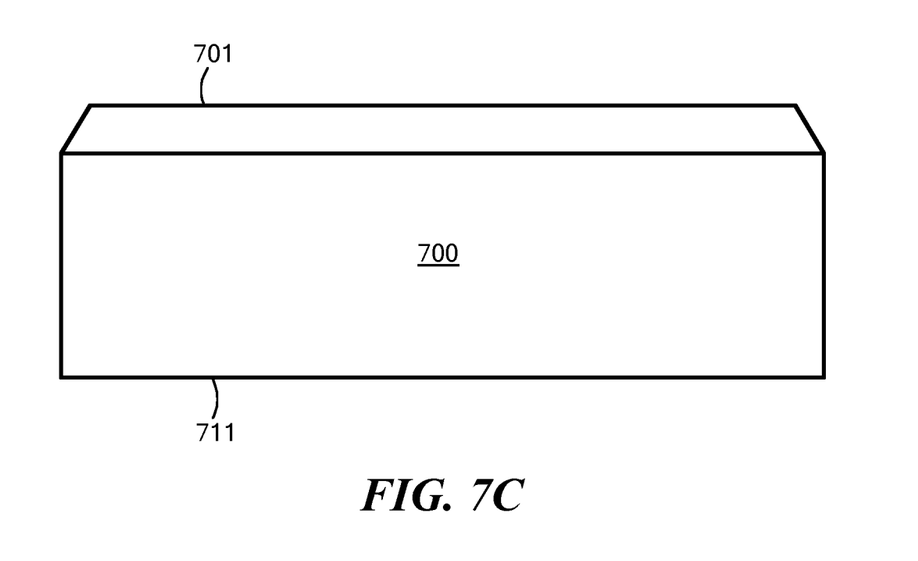

FIGS. 7A-7C schematically illustrate a compression block 700 in accordance with illustrative embodiments. The block 700 is solid, and in some embodiments is somewhat compressible. As a somewhat compressible member, the face of the block 700 preferably conforms to some extent with a facing surface of the portion of the patient to which it applies a pressure. The block 700 is not pneumatic, e.g., it is not an inflatable or deflatable bladder. Moreover, the block 700 is not formed from or include ice, which the inventors believe would be too hard and possibly injure the patient. In some embodiments, the compression block 700 may be made of gel foam, polystyrene foam (e.g., STYROFOAM), or other appropriate material can be placed to enhance the compression/pressure applied to the local area, as described further below.

The inventors have found that a solid compression block provides advantages over a bladder. For example, an inflatable bladder requires additional components, such as a pump mechanism to inflate the bladder, and a release mechanism to deflate the bladder. Such mechanisms increase the cost and complexity of the bladder, while decreasing the bladder's reliability and ease of use. In contrast, a solid block 700 is simple, durable, and reliable.

Moreover, the inventors believe that a bladder (whether inflatable or otherwise) deforms with an increase of internal pressure, and/or pressure against the patient, resulting a variable, and less precise pressure gradient and distribution or dispersal of pressure against the patient. Such an undesirable distribution of pressure can cause complications or impede the healing process. In contrast, pressure applied by a block 700 is more readily focused on a desired area, with less distortion and uncertainty.

As compared to a bladder, a solid block 700 may provide a more effective pressure suited to patient comfort.

For example, the location of pressure applied to a patient by a solid block 700 results in part from the size of the surface of the block that faces the patient. To that end, embodiments of block 700 may have surfaces of varying shapes and sizes.

Figure 7D:
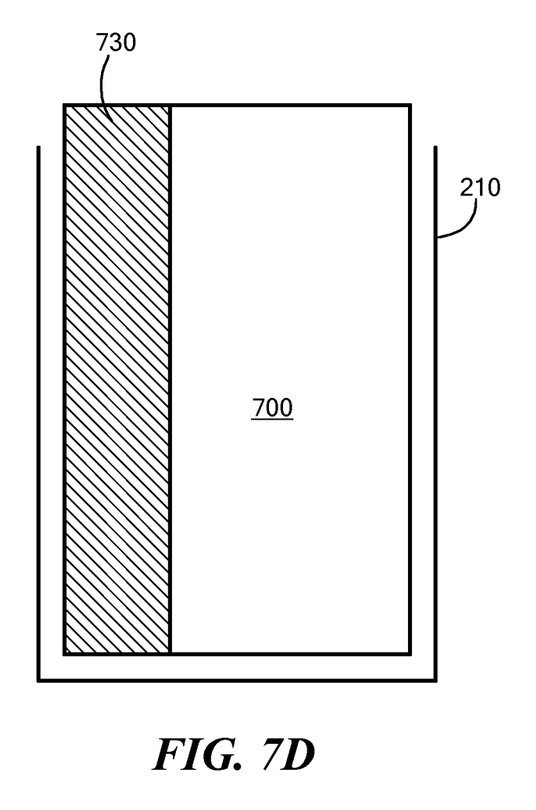
Figure 7E:
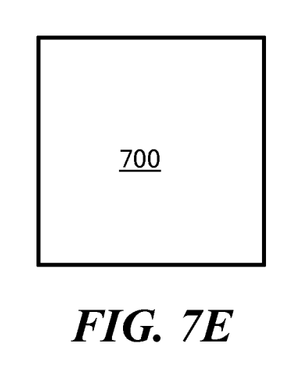
FIGS. 7E-7F schematically illustrate cross sections of embodiments of compression blocks.
Figure 7F:
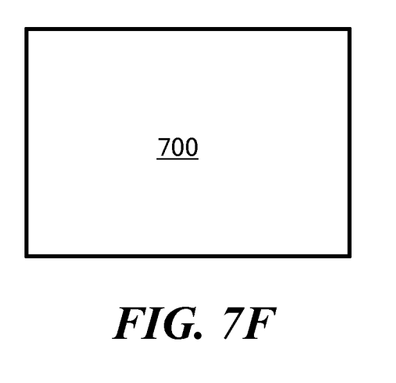
Figure 7G:
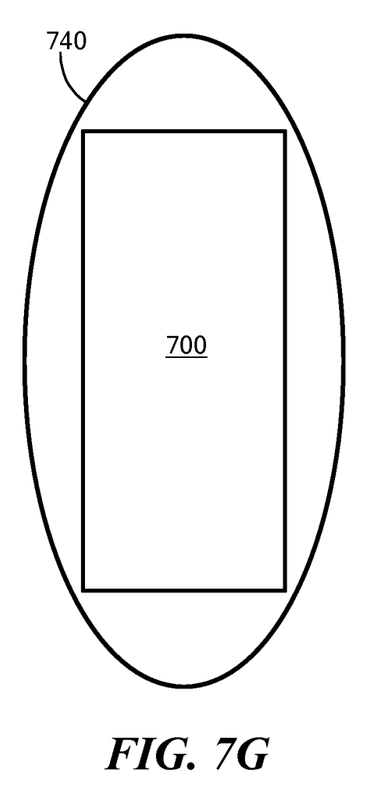
FIG. 7G schematically illustrates an embodiment of a compression block in a sheath.

In some embodiments, the block 700 has a square or rectangular cross section, as schematically illustrated in FIG. 7E and FIG. 7F, respectively, while in other embodiments, the block 700 has a trapezoidal cross section as schematically illustrated in FIG. 7A. For example, the top 701 of the block 700 may have the shape of the frustum of a pyramid. The height and length of the block 700 may be selected so as to cover the incision 650 and/or suture 651.

Illustrative embodiments of the block 700 have multiple surfaces, such as base surface 711, and narrower top surface 701. The localized area of pressure applied to the patient depends on which of those surfaces faces the patient. For example, a surface of the block 700 to be positioned facing the patent may be determined by a user based on the size of the incision 650, the suture 651, and/or the size of the desired localized area 655.

Further, in some embodiments, the pressure applied to a patient by a solid block 700 results in part from the interaction of the block 700 with pliable nature of the material of a garment 100. For example, pressure applied to the localized area may be determined at least in part by the elasticity of the garment, the position of straps, and the surface area of the block. In some embodiments, in which the material of the garment is elastic, the pressure delivered to the patent depends in part on the force applied by the fabric, and the compressibility of the block 700.

In some embodiments, the material selected for the compression block 700 may be foamed polystyrene. For example, the block may be an arteriotomy pressure point pad available from Steri-Systems Corp., P.O. Box 909, 1314 Fouth Avenue, Auburn, Ga. 30011 (Mfg. SKU: 100W; National Stock Number (NSN) 6515-01-464-2574). The density of the foamed polystyrene may vary. In preferred embodiments, material with 1 pound per cubic foot may be selected. However, preferred embodiments could vary density, such as from 0.5 to 1.5 pounds per cubic foot.

In some embodiments, the block 700 is non-compressible, or minimally compressible. If the block is too hard (e.g., steel; ice), the block 700 may fail to conform at all to the surface of the patient, and/or it may dig into the patient and distort the application of applied pressure.

To that end, in some embodiments, a minimally compressible block 700 may by a firm polystyrene material, or another material having a Young's modulus of between $2.0 \times 10^{-10}$ dynes/cm$^2$ and $5.0 \times 10^{-10}$ dynes/cm$^2$, and may be a polystyrene having a Young's modulus of $3.43 \times 10^{-10}$ dynes/cm$^2$. In some embodiments, the block 700 may have a Young's modulus similar to that of polystyrene at 3 to 3.5 GPa. As another example, the block 700 of some embodiments may have a Young's modulus similar to that of Dow Chemical Company's Styrofoam Highload 60 product has a vertical compressive strength of 60 psi (pounds per square inch), meaning that the product experiences 10% deformation under 60 psi of pressure.

FIG. 7D schematically illustrates an embodiment that includes a filler block 730 configured to fit into a garment pouch, e.g., 210, alongside a compression block 700. When placed in a garment pouch, e.g., 210, a filler block 730 occupies space within the garment pouch 210 and forces the compression block 700 to one side or another of the garment pouch 210, thereby allowing adjustment and fine-tuning of the position of the compression block 700 relative to the garment 100, and relative to the localized area 655. In some embodiments, two or more filler blocks 730 may be used to position a compression block 700 within a pouch 210.

Figure 8:
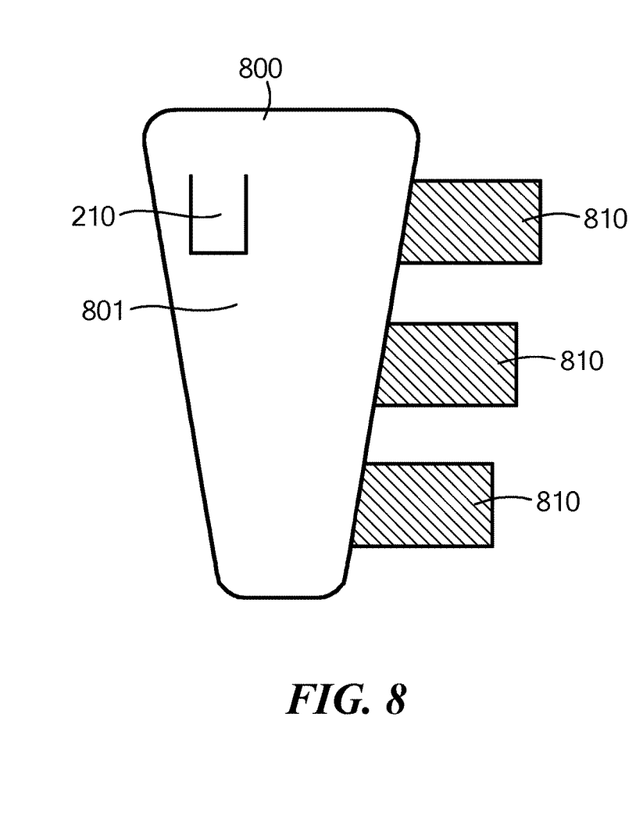
FIG. 8 schematically illustrates an embodiment of a compression sleeve.

FIG. 8 schematically illustrates an alternative embodiment in which the garment 100 is in the form of a compression sleeve 800. The sleeve 800 of this embodiment is configured to wrap around a patient's limb, such as an arm or leg, and to be secured in position by one or more straps 810. The compression sleeve 800 includes a pouch 210 on an inner surface 801 for securing a compression block 700 between the inner surface 801 and the patient. In some embodiments, the sleeve 800 includes a stretchy material to apply pressure to the compression block 700, as described above in connection with the vest 100.

Figure 9:
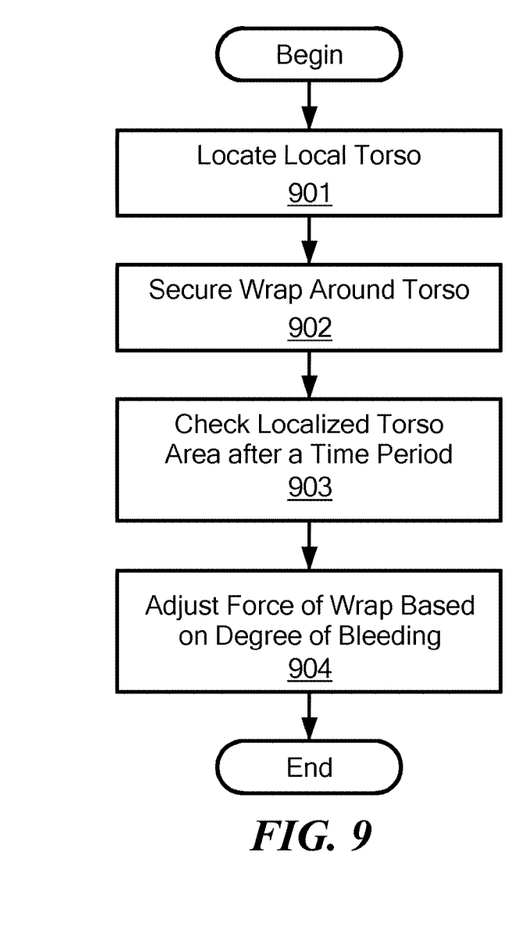
FIG. 9 is a flow chart illustrating a method of using a garment.

FIG. 9 is a flow chart illustrating a method of using a garment to selectively apply pressure to a localized area of a patient's body. The method may explain, for example, a method of mitigating pocket bleeding and hematoma formation in a patient.

The process begins at step 900, in which a medical professional or other user locates a localized area 655 of the patient's body (e.g., FIGS. 6A-6D). For example, the localized area 655 may be over a patient's incision 650, or a suture 651 closing an incision in the patient's torso. The localized torso area has a topography, and may be at least in part covered by a bandage and/or dressing.

Next, step 902 secures a pliable wrap (i.e., the garment 100) around the torso of the patient as discussed above. To that end, the garment 100 is secured so that the block is aligned with the part of the patient's torso requiring pressure. Among other things, as noted above, the patient may have undergone surgery to receive an implantable device. Accordingly, the garment 100 is oriented so that the block is over at least a part of the patient's torso needing the pressure. At this point in the process, the block is between the patient's body (e.g., the bandage and/or dressing 355) and the wrap.

The wrap thus applies a force to the solid block, which produces a corresponding pressure on the localized torso area. This force is due to the cooperation of the material forming the wrap and straps, as well as the material properties of the block. The medical professional ensures that the force is neither too high nor too low. Specifically, the force preferably is high enough to cause the pressure to hinder blood flow to the localized torso area. Accordingly, such a force should minimize or eventually stop bleeding at the local site. Importantly, however, the pressure also preferably is low enough to cause the pressure to permit blood flow to the localized torso area. In some embodiments, the force may be in a sufficient amount to cause the face of the block adjacent to the body to conform to some extent to the topography of at least a portion of the local region. This may further enhance the effect and controllability on hematomas and blood flow.

After the wrap has been secured for some prescribed amount of time (e.g., 30-90 minutes), a medical professional may check the progress of the localized torso area (step 903).

To that end, the medical professional may remove the wrap to view the localized torso area after the prescribed time period. If the medical professional recognizes fluid discharge from the localized torso area, then the wrap may not have been secured with a sufficient force. In that case, the process continues to step 904, in which the medical professional re-secures the wrap with a greater force than the force applied when initially secured. This greater force preferably is high enough to produce a greater block pressure to hinder blood flow to the localized torso area, but again, low enough to cause the pressure to permit blood flow to the localized torso area. Of course, when re-secured, the medical professional secures the wrap so that the block aligns with the local torso area being treated.

Alternatively, if in his/her professional judgement the local area is not bleeding/discharging fluid too much, then the medical professional will re-secure the wrap in the same manner (i.e., aligning the block with the local area) at approximately the same force.

Although the method illustrated by the flow chart in FIG. 9 is directed to a garment for use on a patient's torso, the method could also be applied to the use of garments on a patient's limb, such as sleeve 800 for example.

The following is a listing of reference numbers used herein:

100: Compression vest
101: Left shoulder portion, or scapular end, of vest
102: Outer surface of vest
103: Left chest pad portion of vest
104: Right chest pad portion of vest
105: Right shoulder portion, or pectoral portion, of vest
110: Waist strap or main body of vest
112: Right end of waist strap
113: Velcro fastener
114: Opposing Velcro fastener
116: Left end of waist strap
202: Inner surface of vest
210: Left pouch
211: Right pouch
220: Waist strap
221: Back flap
222: Front flap
350: Surface of patient's body
355: Bandage or dressing
360: Gradient graph
361: Pressure point
362: Lesser pressure point
650: Incision site
651: Suture
655: Localized area
700: Compression block
701: Top of compression block
711: Bottom of compression block
730: Filler block
740: Sheath
800: Sleeve
801: Inner surface of sleeve
810: Sleeve straps Accordingly, unlike a tourniquet, when secured to the patient, the pressure that the garment applies is not sufficient to completely prevent blood flow. Rather, the garment applies a pressure sufficient to hinder but not completely prevent blood flow in the localized area 655 of the patient's body.

It is expressly understood that many other embodiments and modifications may be contemplated as included within the apparatus although not specifically illustrated. For example, it may be expressly contemplated that VELCRO fasteners may be placed in different positions or switched, namely a felt fastener exchange for hook fastener and vice versa. In a similar manner, although VELCRO may be preferred attachment means, any other appropriate attachment means, including bonded pressure adhesives, now known or later devised, may also be equivalently substituted. Still further, although it may be expressly contemplated that no strap, tape, or other means may be necessary to secure the compression block to the vest 100, the inclusion of such elements in some embodiments may be contemplated.

Complementary VELCRO fasteners can also be provided on the outside ends of the waist band 110 so that waist band 110 can be stretched and overlapped at its opposing ends and thus connected together.

Although the above discussion discloses various exemplary embodiments, it should be apparent that those skilled in the art can make various modifications that may achieve some of the advantages of the embodiments described herein without departing from the true scope of the inventive concepts. All such variations and modifications are intended to be within the scope of the present inventions as defined in any appended claims.

What is claimed is:

1. A method of mitigating pocket bleeding and hematoma formation in a patient, the method comprising:
    locating a localized torso area of the patient that may be subject to bleeding and/or hematoma formation, the localized torso area being at least in part covered by a bandage and/or dressing;
    providing a pliable wrap configured to couple with a non-inflatable block;
    securing the pliable wrap around a torso of the patient;
    adjusting a position of the non-inflatable block within a pouch of the pliable wrap to align the non-inflatable block with the located localized torso area, the non-inflatable block being secured between i) at least a portion of the wrap and ii) the bandage and/or dressing at least in part covering the localized torso area; and
    securing further comprising causing the wrap to apply a force to the non-inflatable block, the force producing a pressure produced by the non-inflatable block on the localized torso area,
    the force applied to the non-inflatable block being high enough to cause the pressure to hinder blood flow to the localized torso area to promote clotting at the localized torso area,
    the force applied to the non-inflatable block being low enough to cause the pressure to permit blood flow to the localized torso area to promote healing.

2. The method as defined by claim 1, wherein the non-inflatable block has a block face configured to apply the pressure to the localized torso area, the localized torso area having a topography, further wherein securing comprises applying the force to the non-inflatable block in a sufficient amount to cause the block face to change its shape to at least in part conform to the topography of the localized torso area.

3. The method as defined by claim 1 wherein the non-inflatable block comprises a thermoplastic polymer.

4. The method as defined by claim 1 wherein the non-inflatable block comprises polystyrene foam.

5. The method as defined by claim 1, further comprising:
    removing the pliable wrap to view the localized torso area after a prescribed time period;
    recognizing fluid discharge from the localized torso area; and
    re-securing the pliable wrap around the torso of the patient with a greater force than the force applied when initially secured, the greater force being high enough to produce a greater pressure produced by the non-inflatable block sufficient to hinder blood flow to the localized torso area, but low enough to cause the pressure to permit blood flow to the localized torso area.

6. The method as defined by claim 1, wherein the pliable wrap comprises an elastic material.

7. The method as defined by claim 1, wherein the pliable wrap comprises neoprene.

8. The method as defined by claim 1, further comprising adjusting one or more straps of the pliable wrap to adjust the force of the pliable wrap to the non-inflatable block.

9. The method as defined by claim 1, further comprising placing the non-inflatable block within the pouch.

10. The method as defined by claim 1, wherein the non-inflatable block has a wedge shape with a narrow face positioned to face the patient when the pliable wrap is secured to the patient.

11. The method as defined by claim 1, wherein adjusting the position of the non-inflatable block relative to the pliable wrap comprises adjusting the position of the non-inflatable block relative to the pliable wrap while the pliable wrap is secured around the torso of the patient.

12. The method as defined by claim 1, wherein adjusting the position of the non-inflatable block relative to the pliable wrap comprises adjusting the position of the non-inflatable block within the pouch to a desired location within the pouch in order to align the block with a particular localized torso area of the patient, the particular localized torso area of the patient being one among a plurality of localized torso areas of the patient over which the block may be placed within the pouch.

13. The method as defined by claim 12, further comprising placing a filler block within the pouch.

14. The method as defined by claim 1, further comprising adjusting an orientation of the non-inflatable block relative to the pliable wrap to increase or decrease an area of the localized torso area over which the pressure produced by the non-inflatable block is applied.

15. The method as defined by claim 14, wherein adjusting the orientation of the non-inflatable block comprises rotating the non-inflatable block such that a different surface of the non-inflatable block faces the patient.

16. The method as defined by claim 1, further comprising:
de-coupling the non-inflatable block from the pliable wrap while the pliable wrap is secured around the torso of the patient; and
re-coupling the non-inflatable block with the pliable wrap while the pliable wrap is secured around the torso of the patient.

17. A method of mitigating pocket bleeding and hematoma formation in a patient, the method comprising:
locating a localized torso area of the patient that may be subject to bleeding and/or hematoma formation, the localized torso area being at least in part covered by a bandage and/or dressing;
providing a pliable wrap having a non-inflatable block coupled with the wrap;
securing the pliable wrap around a torso of the patient to align the non-inflatable block with the located localized torso area, the non-inflatable block being secured between i) at least a portion of the wrap and ii) the bandage and/or dressing at least in part covering the localized torso area; and
securing further comprising causing the wrap to apply a force to the non-inflatable block, the force producing a pressure produced by the non-inflatable block on the localized torso area,
the force applied to the non-inflatable block being high enough to cause the pressure to hinder blood flow to the localized torso area to promote clotting at the localized torso area,
the force applied to the non-inflatable block being low enough to cause the pressure to permit blood flow to the localized torso area to promote healing;
removing the pliable wrap to view the localized torso area after a prescribed time period;
recognizing fluid discharge from the localized torso area; and
re-securing the pliable wrap around the torso of the patient with a greater force than the force applied when initially secured, the greater force being high enough to produce a greater pressure produced by the non-inflatable block sufficient to hinder blood flow to the localized torso area, but low enough to cause the pressure to permit blood flow to the localized torso area.

* * * * *